US008192700B2

(12) United States Patent
Minemura (10) Patent No.: US 8,192,700 B2
(45) Date of Patent: Jun. 5, 2012

(54) TISSUE PIECE TREATING APPARATUS (75) Inventor: Hiroyuki Minemura, Chikuma (JP)

(73) Assignees: Sakura Seiki Co., Ltd., Nagano (JP); Sakura Finetek Japan Co., Ltd., Tokyo (JP)

( * ) Notice: Subject to any disclaimer, the term of this patent is extended or adjusted under 35 U.S.C. 154(b) by 94 days.

(21) Appl. No.: 12/989,701

(22) PCT Filed: May 18, 2009

(86) PCT No.: PCT/JP2009/059135
§ 371 (c)(1),
(2), (4) Date: Oct. 26, 2010

(87) PCT Pub. No.: WO2009/142174
PCT Pub. Date: Nov. 26, 2009

(65) Prior Publication Data
US 2011/0039328 A1  Feb. 17, 2011

(30) Foreign Application Priority Data

May 19, 2008  (JP) .................................. 2008-131278

(51) Int. Cl.
*A61B 10/00* (2006.01)
(52) U.S. Cl. .......... 422/536; 422/50; 422/500; 422/501; 422/502; 436/180
(58) Field of Classification Search ............ 422/50, 422/500–502, 536; 436/180
See application file for complete search history.

(56) References Cited

FOREIGN PATENT DOCUMENTS

| JP | 11271194 | 10/1999 |
|----|----------|---------|
| JP | 2001122382 | 5/2001 |
| JP | 2001124679 | 5/2001 |

OTHER PUBLICATIONS

Sakura Seiki Co., Ltd., et al., International Search Report dated Aug. 11, 2010 for International Application No. PCT/JP2009/059135.

*Primary Examiner* — Jyoti Nagpaul
(74) *Attorney, Agent, or Firm* — Blakely Sokoloff Taylor & Zafman LLP (57) ABSTRACT

The present invention can solve such a problem that a conventional tissue piece treating apparatus has difficulty of reduction in size and restriction on installation and stopping subsequent treatment operations when the amount of chemical supplied to a processing chamber is insufficient. The tissue piece treating apparatus comprises: new chemical tanks 15, 17 being integrally attached to both sidewall faces of a main body of the apparatus respectively, having larger capacities than a plurality of chemical tanks 14, 16 in which chemicals with different concentrations are stored for performing immersion treatment of a tissue piece accommodated in a processing chamber 12, having inner wall faces respectively reinforced by reinforcing members, and storing unused new chemicals of the same types as the chemicals stored in the chemical tanks 14, 16; pipes being extended from the new chemical tanks 15, 17 and connected to a selection valve 30 so as to supply the new chemicals stored in the new chemical tanks 15, 17 to the processing chamber 12; and a control section 38 controlling the selection valve 30, an open/close valve 32 and a pump 34 so as to supply the new chemical of an amount corresponding to an insufficiency of the amount of the chemical supplied from the new chemical tanks 15,17 to the processing chamber 12 when a detection sensor 36 detects that the amount of the chemical supplied to the processing chamber 12 is insufficient.

8 Claims, 9 Drawing Sheets

TISSUE PIECE TREATING APPARATUS

CROSS-REFERENCE TO RELATED APPLICATION

This is a non-provisional application claiming the benefit of International Patent Application No. PCT/JP2009/059135 filed May 18, 2009.

FIELD OF TECHNOLOGY

The present invention relates to a tissue piece treating apparatus, more precisely relates to a tissue piece treating apparatus capable of performing prescribed treatment for producing a microscopic specimen of a tissue piece taken from a living body.

BACKGROUND TECHNOLOGY

In hospitals and laboratories, tissue piece treating apparatuses, in each of which tissue pieces are automatically fixed, dehydrated, degreased, replaced and embedded in paraffin, are used for producing microscopic specimens of tissue pieces taken from living bodies.

Figure 9:
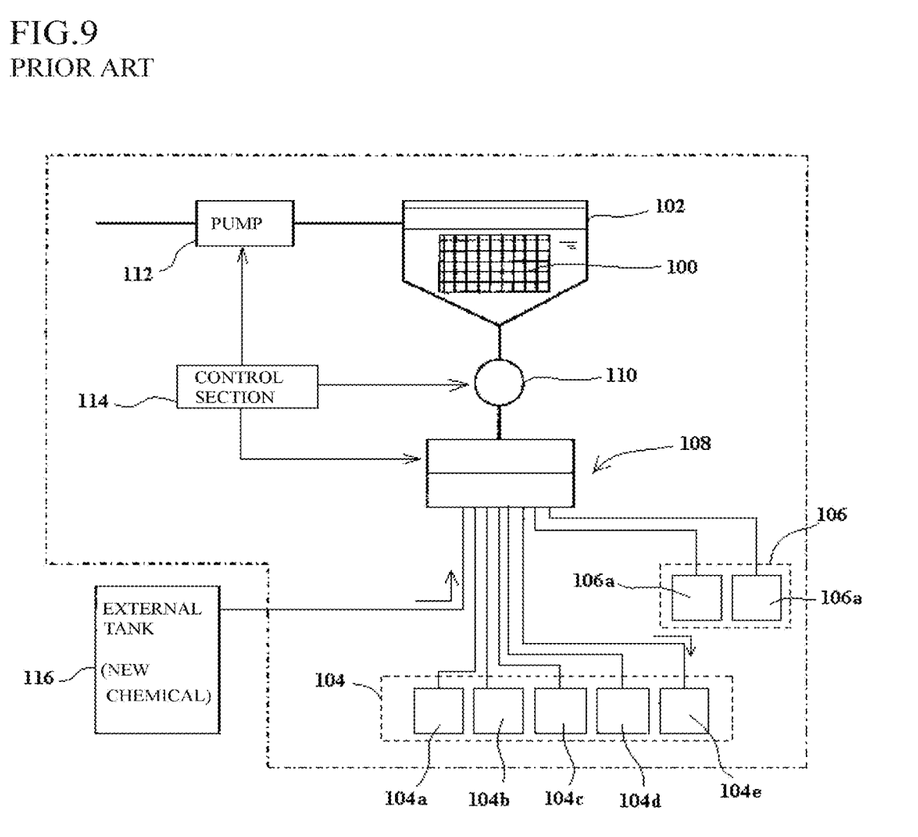
[FIG. 9] It is an explanation view of the conventional tissue piece treating apparatus.

For example, a conventional tissue piece treating apparatus is disclosed in the following Patent Document 1, and the apparatus is shown in FIG. 9.

In the tissue piece treating apparatus shown in FIG. 9, a main body of the apparatus includes: a processing chamber 102 accommodating baskets 100, in which tissue pieces are inserted; a plurality of chemical tanks 104a-104e being mounted on a rack and storing chemicals, with sequentially different concentrations, for performing immersion treatment of the tissue pieces in the baskets 100; and paraffin tanks 106a and 106b accommodated in a heat-retaining chamber 106. Temperatures of the chemicals in the chemical tanks 104a-104e are 104a<104b<104c<104d<104e.

Each of the chemical tanks 104a-104e and the paraffin tanks 106a and 106b is connected to a rotary valve 108 provided to the main body as a selection valve, and the rotary valve 108 is connected to the processing chamber 102 via an open/close valve 110.

With this structure, each of the chemical tanks 104a-104e and the paraffin tanks 106a and 106b is selectively connected to the processing chamber 102 by the rotary valve 108.

Further, inner pressure of the processing chamber 102 is increased and reduced by a pump 112, and the chemical or paraffin can be supplied to the processing chamber 102 from one of the chemical tanks 104a-104e and the paraffin tanks 106a and 106b, which is selected by the rotary valve 108.

The chemical or paraffin, which has been supplied to the processing chamber 102 and contacted the tissue pieces in the basket 100, is returned to the original tank by increasing the inner pressure of the processing chamber 102.

Since the rotary valve 108, the open/close valve 110 and the pump 112 are controlled by a control section 114, the tissue pieces can be immersed in the predetermined chemicals and the paraffin according to predetermined treatment sequence, which has been previously stored in the control section.

In the tissue piece treating apparatus shown in FIG. 9, an external tank 116 is located outside of the main body. An unused new chemical for treating the tissue pieces is stored in the external tank 116. The external tank 116 is connected to the rotary valve 108.

When the chemicals stored in the chemical tanks 104a-104b are used for the immersion treatment of the tissue pieces several times, each of the chemicals stored in the chemical tanks 104a-104b is transferred to the chemical tank in which the chemical, whose concentration is lower than and proximate to that of the chemical to be transferred, has been stored.

In the transferring process, firstly the chemical tank 104a, in which the chemical used for the immersion treatment of the tissue pieces the most times, including moisture from the tissue pieces and having the lowest concentration is stored, is detached from the main body, a vacant chemical tank 104a is attached thereto, and the chemical stored in the chemical tank 104b is transferred to the vacant chemical tank 104a via the rotary valve 108, the open/close valve 110 and the processing chamber 102.

Further, the chemical stored in the chemical tank 104c is transferred to the vacant chemical tank 104b via the rotary valve 108, the open/close valve 110 and the processing chamber 102. Namely, the chemicals are transferred to the adjacent chemical tanks as well, and finally the chemical tank 104d is evacuated.

The new chemical stored in the external tank 116 is transferred to the vacant chemical tank 104d via the rotary valve 108, the open/close valve 110 and the processing chamber 102.

Patent Document 1: Japanese Laid-open Patent Publication No. 2001-124679

DISCLOSURE OF THE INVENTION

In the tissue piece treating apparatus shown in FIG. 9, the transferring process of the chemicals can be automatically performed after detaching the chemical tank 104a.

However, the external tank 116 is provided outside of the main body of the tissue piece treating apparatus, so the apparatus must grow in size and an installation location of the apparatus must be limited by the location of the external tank 116.

In the tissue piece treating apparatus shown in FIG. 9, amounts of the chemicals stored in the chemical tanks are gradually reduced, by evaporation and penetrating into tissue pieces, while repeating the treatment of tissue pieces, so a prescribed amount of the chemical cannot be supplied to the processing chamber 102 sometimes. Usually the chemical whose concentration is higher than and proximate to that of the chemical in the processing chamber 102 is supplied from the chemical tank to the processing chamber 102 so as to completely immerse the tissue pieces in the chemical stored in the processing chamber 102, and then the subsequent treatment operations are stopped. In case of sequentially refilling the chemical tank with the chemical from another chemical tank, an amount of the chemical for refilling the chemical tank will be insufficient when the chemical with the highest concentration is supplied from the chemical tank to the processing chamber 102.

Even if important tissue pieces can be effectively protected by immersing the tissue pieces in the chemical stored in the processing chamber 102 and stopping the subsequent treatment operations, but the subsequent treatment operations cannot performed, so the sequence of the treatment of the tissue pieces cannot be completed by estimated time. If microscopic specimens cannot be produced by the estimated time, diagnosis must be postponed.

An object of the present invention is to provide a tissue piece treating apparatus capable of solving the problems of the conventional tissue piece treating apparatus, i.e., downsizing is difficult, an installation location is limited and subsequent treatment operations must be stopped when an amount of the chemical supplied to the processing chamber is insufficient, so the tissue piece treating apparatus of the present invention is capable of being downsized, improving flexibility of an installation location and carrying on treatment operations even if an amount of the chemical supplied to the processing chamber is insufficient.

MEANS FOR SOLVING THE PROBLEMS

To solve the above described problems, the inventor of the present invention thought that it is effective to integrally attach a new chemical tanks to a sidewall face of a main body of the apparatus and supply a new chemical of an amount corresponding to an insufficiency of the amount of the chemical from the new chemical tank to the processing chamber, so that the inventor reached the present invention.

The tissue piece treating apparatus of the present invention comprises: a processing chamber for accommodating a tissue piece; a plurality of chemical tanks storing chemicals with sequentially different concentrations for performing immersion treatment of the tissue piece: a selection valve for connecting the processing chamber to the selected chemical tank: an open/close valve being provided to a pipe connecting the selection valve to the processing chamber so as to open/close the pipe; a pump for increasing and reducing inner pressure of the processing chamber; a detection sensor for detecting that a prescribed amount of the chemical is supplied to the processing chamber; and a control section being attached to a main body of said apparatus, the control section controlling the selection valve, the open/close valve and the pump so as to supply the chemical stored in the selected chemical tank to the processing chamber, whose inner pressure has been reduced by the pump, via the open/close valve and so as to discharge the chemical, which has been used for performing immersion treatment of the tissue piece, from the processing chamber, whose inner pressure has been increased by the pump, and return the same to the selected chemical tank via the selection valve, thereby the immersion treatment of the tissue piece can be performed in the chemicals from the lowest concentration to the highest concentration sequentially, new chemical tanks are integrally attached to a sidewall face of the main body, the new chemical tanks have larger capacities than the chemical tanks, store unused new chemicals of the same types as the chemicals stored in the chemical tanks and have inner wall faces respectively reinforced by reinforcing members so as to prevent deformation of the new chemical tanks when inner pressure is reduced and increased for supplying and discharging the new chemical, pipes from the new chemical tanks are connected to the selection valve so as to supply the new chemicals stored in the new chemical tanks to the processing chamber, and the control section controls the selection valve, the open/close valve and the pump so as to supply the new chemical of an amount corresponding to an insufficiency of the amount of the chemical from the new chemical tank to the processing chamber when a detection sensor detects that the amount of the chemical supplied to the processing chamber is insufficient, thereby the immersion treatment can be continued.

In the present invention, the control section controls the selection valve, the open/close valve and the pump so as to supply the chemical, whose concentration is higher than and proximate to that of the chemical in the processing chamber and whose amount corresponds to an insufficiency of the amount of the chemical in the processing chamber, from the chemical tank to the processing chamber when the detection sensor detects that the amount of the chemical supplied to the processing chamber is insufficient, to continue the immersion treatment, and so as to supply the new chemical of the amount corresponding to an insufficiency of the amount of the chemical in the processing chamber from the new chemical tank to the processing chamber when the chemical with the highest concentration is supplied from the chemical tank to the processing chamber and the detection sensor detects that the amount of the chemical supplied to the processing chamber is insufficient, thereby the immersion treatment can be continued, and concentration gradient of the chemicals stored in the chemical tanks can be maintained.

In the apparatus, the control section controls the selection valve, the open/close valve and the pump so as to return the chemical, to which the chemical or new chemical of the amount corresponding to the insufficiency has been added and in which the immersing treatment of the tissue piece has been performed, to the chemical tank of the insufficient chemical, thereby the chemical tank of the insufficient chemical can be easily refilled with the chemical.

In the apparatus, the control section controls the selection valve, the open/close valve and the pump so as to sequentially supply the chemicals stored in the chemical tanks to the processing chamber, in which the tissue piece is accommodated, according to the treatment process, to perform the immersion treatment of the tissue piece, sequentially transfer the chemicals to the predetermined chemical tanks, supply the new chemical stored in the new chemical tank to the processing chamber to perform the immersion treatment of the tissue piece and then transfer the new chemical, which has been used for the immersion treatment, to the chemical tank of the chemical with the highest concentration, when the chemical with the lowest concentration is discharged from the chemical tank and each of the chemicals stored in the chemical tank is sequentially transferred to the chemical tank of the chemical whose concentration is lower than and proximate to that of the chemical to be transferred, thereby the chemicals can be transferred automatically.

In the apparatus, each of the new chemical tanks has means for solely supplying the new chemical, thereby the chemical tanks can be easily refilled with the new chemical.

In the apparatus, the main body has a supply port, which is provided to one end of a pipe for supplying the new chemical to the new chemical tank, and a supply/discharge port, which is provided to one end of another pipe whose the other end is connected to the selection valve so as to supply the chemical to the processing chamber and discharge the same therefrom via the selection valve, thereby refilling the new chemical tank with the new chemical, supplying the chemical to the processing chamber and discharging the chemical therefrom can be easily performed by the supply port and the supply/discharge port of the main body.

Further, in the apparatus, the chemicals with different concentrations are stored in the plurality of chemical tanks for performing the immersion treatment of the tissue piece, and the new chemical tanks, which store the two unused new chemicals of the same types as the chemicals, are respectively attached to the both sidewall faces of the main body, thereby the tissue piece can be effectively treated with the two chemicals and the main body can be stabilized by attaching the new chemical tanks to the both sidewall faces.

EFFECTS OF THE INVENTION

In the tissue piece treating apparatus of the present invention, the new chemical tanks are integrally attached to the sidewall face of the main body, the new chemical tanks have larger capacities than the chemical tanks and have the inner wall faces respectively reinforced by the reinforcing members. With this structure, even if the inner pressure of the new chemical tanks are reduced and increased when the new chemicals are supplied to and discharged from the new chemical tanks or the inner pressure of the new chemical tanks are increased when large amounts of the new chemicals are supplied to the new chemical tanks, the deformation of the new chemical tanks can be prevented, further the tissue piece treating apparatus can be downsized and flexibility of installation can be improved.

In the present invention, the new chemical of the amount corresponding to the insufficiency of the amount of the chemical in the processing chamber is supplied from the new chemical tank to the processing chamber when the amount of the chemical supplied to the processing chamber is insufficient, thereby the immersion treatment and the subsequent treatments can be carried on. Therefore, the tissue piece can be treated within a prescribed time, and the microscopic specimen can be produced by estimated time.

In case that the amount of the chemical supplied to the processing chamber is insufficient, the chemical, whose concentration is higher than and proximate to that of the chemical in the processing chamber and whose amount corresponds to the insufficiency of the amount of the chemical in the processing chamber, is supplied from the chemical tank to the processing chamber, so that the immersion treatment of the tissue piece can be carried on in the processing chamber and the subsequent treatment operations also can be carried on. In this case, when the chemical with the highest concentration is supplied from the chemical tank to the processing chamber, the amount of the chemical supplied to the processing chamber is insufficient, thus the new chemical of the amount corresponding to the insufficiency of the amount of the chemical is supplied from the new chemical tank to the processing chamber, thereby the immersion treatment and the subsequent treatment operations can be carried on. Therefore, the tissue piece can be treated within a prescribed time, and the microscopic specimen can be produced by estimated time.

BRIEF DESCRIPTION OF THE DRAWINGS

[FIG. 1]

[FIG. 5]

[FIG. 6]

[FIG. 7]

EMBODIMENTS OF THE INVENTION

Figure 1A:
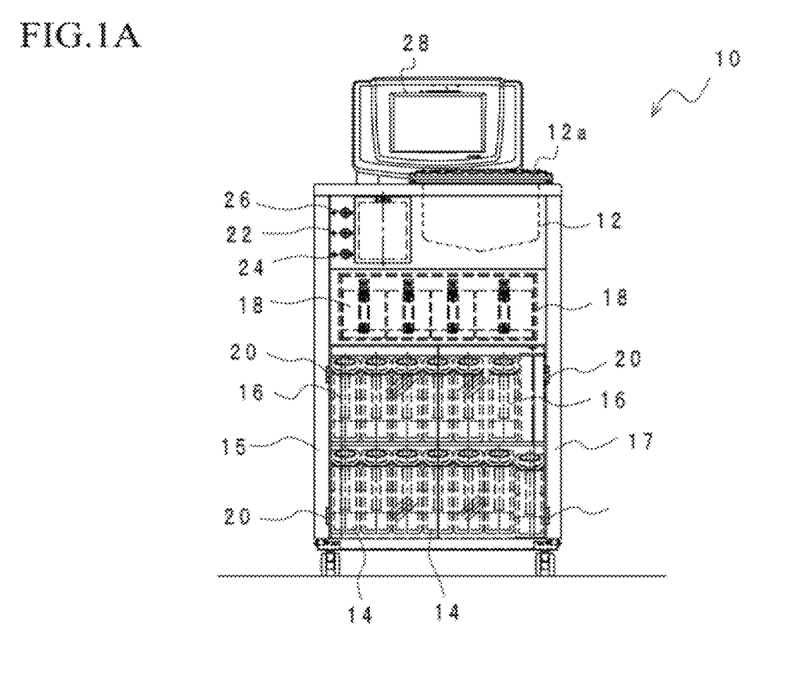
FIG. 1A is a front view of an embodiment of the tissue piece treating apparatus of the present invention.
Figure 1B:
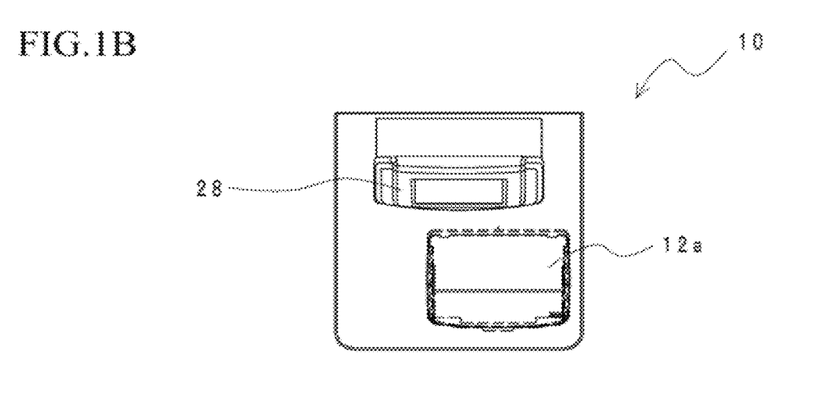
FIG. 1B is a plan view thereof.

An embodiment of the tissue piece treating apparatus of the present invention is shown in FIGS. 1A and 1B. FIG. 1A is a front view of the tissue piece treating apparatus, and FIG. 1B is a plan view thereof.

In the tissue piece treating apparatus shown in FIGS. 1A and 1B, a processing chamber 12, in which baskets storing tissue pieces are accommodated, is opened and closed by a lid 12a. In the processing chamber 12, moisture in the tissue pieces is replaced by ethanol, and then xylene is supplied to replace ethanol in the tissue pieces by xylene, further molten paraffin is supplied to replace xylene in the tissue pieces by paraffin. Thus, a plurality of chemical tanks 14, 14 . . . , in which ethanol to be supplied to the processing chamber 12, with different concentrations, are stored respectively, are arranged in a lowermost part of a main body of the apparatus, which includes the processing chamber 12, and a plurality of chemical tanks 16, 16 . . . , in which xylene to be supplied to the processing chamber 12, with different concentrations, are stored respectively, are arranged in a second part above the lowermost part, in which the chemical tanks 14, 14 . . . are arranged.

Further, a plurality of chemical tanks 18, 18 . . . , in which molten paraffin to be supplied to the processing chamber 12 are stored respectively, are arranged in a third part above the second part, in which the chemical tanks 16, 16 . . . are arranged. The part accommodating the chemical tanks 18, 18 . . . is a heat-retaining chamber capable of maintaining a molten state of paraffin. Capacity of the rightmost tank 18 of the chemical tanks 18, 18 . . . is larger than that of other chemical tanks 18, 18 . . . , and molten paraffin is stored therein.

A new chemical tank 15, whose capacity is larger than that of the chemical tanks 14, 14 . . . (e.g., twice or three times as large as the capacity of the chemical tanks 14, 14 . . . ) and in which unused new ethanol (new chemical) is stored, is integrally attached to one of sidewall faces of the main body, in which the plurality of chemical tanks storing the chemicals are arranged; a new chemical tank 17, whose capacity is larger than that of the chemical tanks 16, 16 . . . (e.g., twice or three times as large as the capacity of the chemical tanks 16, 16 . . . ) and in which unused new xylene (new chemical) is stored, is integrally attached to the other sidewall face of the main body. By integrally attaching the new chemical tanks 15 and 17 to the both sidewall faces, structural strength of the apparatus can be improved.

Figure 2:
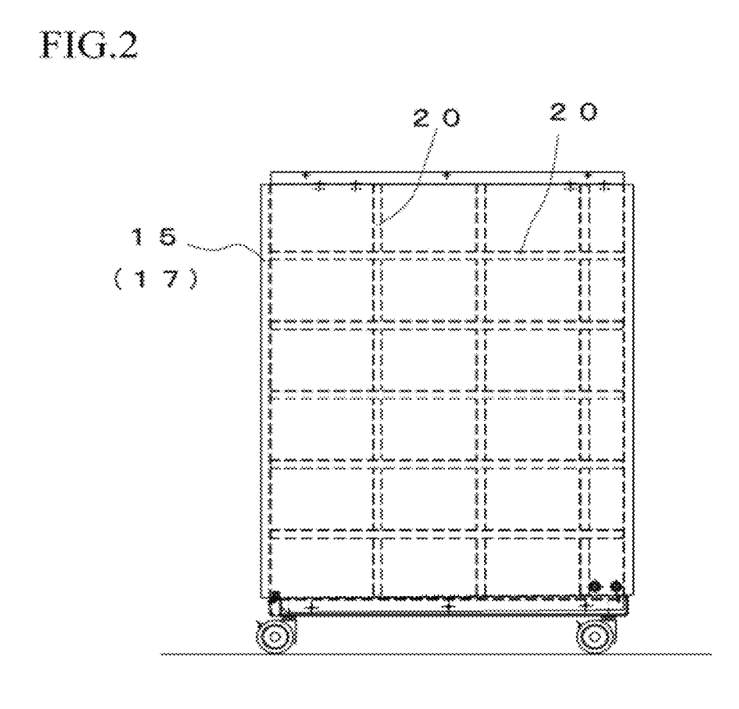
[FIG. 2] It is an explanation view of a new chemical tank of the apparatus shown in FIGS. 1A and 1B, which explains a manner of reinforcement.

The new chemical tanks 15 and 17 have capacities larger than those of the chemical tanks 14, 14 . . . and 16, 16 . . . and is slimmer than the chemical tanks. As shown in FIG. 2, an inner wall face of each of the new chemical tanks 15 and 17 is reinforced by reinforcing members 20, 20 . . . , which are bonded crosswise. By reinforcing the inner wall face with the reinforcing members 20, 20 . . . , even if inner pressure of the new chemical tanks 15 and 17 are reduced when the new chemicals are supplied to the new chemical tanks or the inner pressure (hydraulic head pressure) of the new chemical tanks are increased when prescribed amounts of ethanol and xylene are supplied to the new chemical tanks, deformation of the new chemical tanks 15 and 17 can be highly restrained.

Supply ports for supplying the new chemicals to the new chemical tanks 15 and 17 and a supply/discharge port for supplying the chemical to the processing chamber 12 and discharging the same therefrom are provided in the front face of the main body of the tissue piece treating apparatus 10.

A display unit 28 is provided on the upper face of the main body of the apparatus 10 so as to show treating statuses of the tissue pieces in the processing chamber 12, etc.

Figure 3:
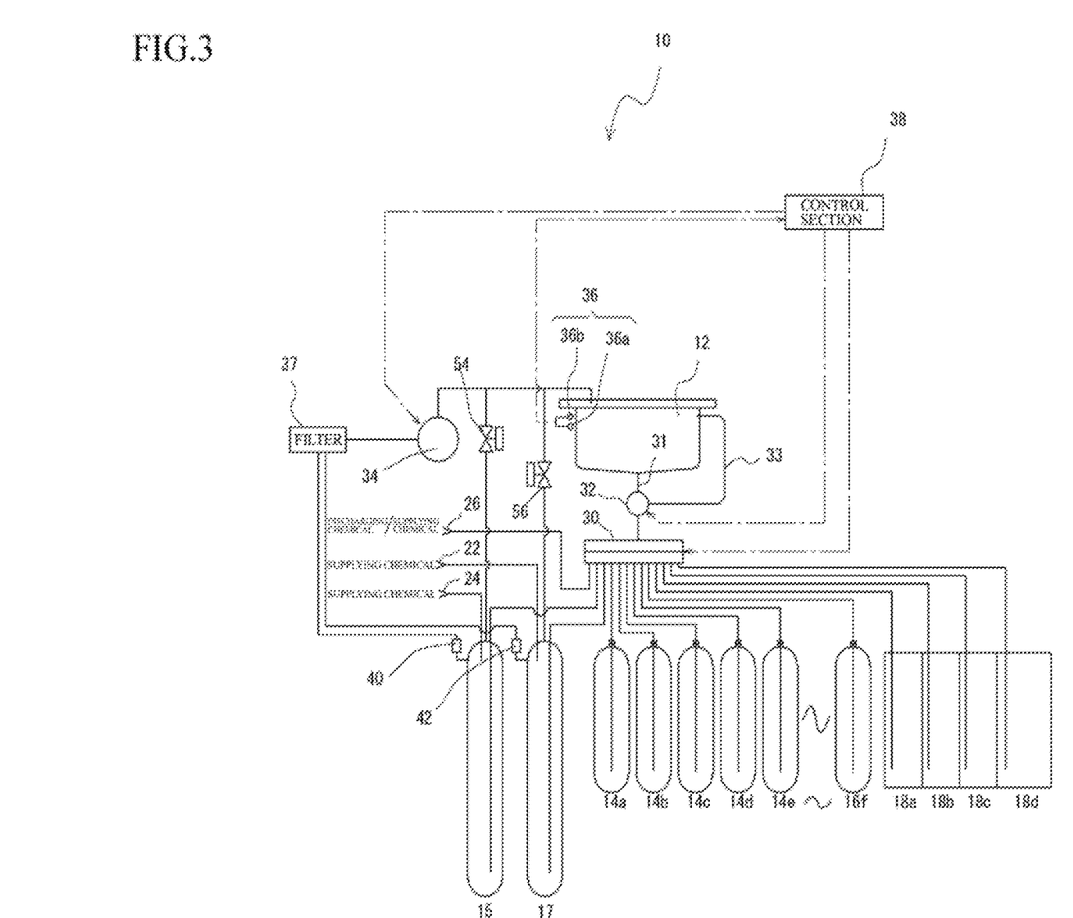
[FIG. 3] It is a schematic diagram of the apparatus shown in FIGS. 1A and 1B.

A schematic diagram of the apparatus 10 shown in FIGS. 1A and 1B is shown in FIG. 3. As shown in FIG. 3, the chemical tanks 14a-14g for storing ethanol and the chemical tanks 16a-16f for storing xylene are accommodated in the main body of the apparatus 10. Further, the chemical tanks 18a-18d for storing molten paraffin are accommodated therein, the capacity of the chemical tank 18d is larger than that of the chemical tanks 18a-18c so as to refill the chemical tanks 18a-18c, in which amounts of molten paraffin have been insufficient, with the molten paraffin of the amount corresponding to the insufficiencies. To supply paraffin to the apparatus, paraffin may be supply to the chemical tank 18d only.

As shown in FIG. 3, a rotary valve 30, which acts as a selection valve, is provided to the main body of the apparatus 10 so as to selectively connect the chemical tank, which is selected from the chemical tanks 14a-14g, 16a-16f and 18a-18d and which store the chemicals with prescribed concentrations, to the processing chamber 12. Concentrations of ethanol stored in the chemical tanks 14a-14g are 14a<14b<14c<14d<14e<14f<14g. Number of times of immersing tissue pieces in the ethanol stored in the chemical tanks 14a-14g and amounts of impurities, e.g., water, fat, included therein are 14a>14b>14c>14d>14e>14f>14g.

Concentrations of xylene stored in the chemical tanks 16a-16f are 16a<16b<16c<16d<16e<16f due to interfusion of ethanol.

The chemical tanks 18a-18d are arranged in the heat-retaining chamber, and concentrations of molten paraffin stored therein are 18a<18b<18c<18d. Number of times of immersing tissue pieces in the paraffin stored in the chemical tanks 18a-18d and amounts of xylene interfused therein are 18a>18b>18c>18d.

An open/close valve 32 is provided midway between a pipe 31, which is connected to a bottom face of the processing chamber 12 and the rotary valve 30, and a pipe 33 is connected to the open/close valve 32 and the upper part of the processing chamber 12. The open/close valve 32 is a three-way valve capable of connecting the pipe 31 to the rotary valve 30 and connecting the pipe 33 to the rotary valve 30.

A pump 34 is capable of increasing and reducing inner pressure of the processing chamber, and the chemical can be supplied to the processing chamber 12 from the prescribed chemical tank, which has been selected by the rotary valve 30, by reducing the inner pressure of the processing chamber 12 by the pump 34 and connecting the prescribed chemical tank to the pipe 33 by the open/close valve 32.

On the other hand, the chemical stored in the processing chamber 12 can be sent to the prescribed tank, which has been selected by the rotary valve 30, by increasing the inner pressure of the processing chamber 12 by the pump 34 and connecting the prescribed chemical tank to the pipe 31 by the open/close valve 32.

Note that, the pump 34 is capable of sucking air through a filter 37 and discharging a gas including chemicals from the processing chamber 12.

The processing chamber 12 has a detection sensor 36 for detecting that a prescribed amount of chemical is supplied thereto. The detection sensor 36 is constituted by a level-securing sensor 36a and an upper limit sensor 36b. The level-securing sensor 36a is used for securing the amount of the chemical in the processing chamber 12 so as to fully immerse the tissue pieces in the chemical; the upper limit sensor 36b is used for detecting upper limit of the amount of the chemical stored in the processing chamber 12.

The new chemical tanks 15 and 17 are respectively integrally attached to the both sidewall faces of the main body including the chemical tanks, the rotary valve 30, the open/close valve 32, etc. The capacity of the new chemical tank 15 is twice or three times as large as that of the chemical tanks 14a-14g, and unused new ethanol is stored therein. The unused new ethanol can be supplied to the new chemical tank 15 via the supply port 24.

The capacity of the new chemical tank 17 is twice or three times as large as that of the chemical tanks 16a-16f, and unused new xylene is stored therein. The unused new xylene can be supplied to the new chemical tank 17 via the supply port 22.

Pressure equalizing lines are provided between the processing chamber 12 and the new chemical tanks 15 and 17, and open/close valves 54 and 56 are respectively provided to the pressure equalizing lines.

The chemicals in the new chemical tanks 15 and 17 are evaporated by outside air temperature, so inner pressures of the new chemical tanks 15 and 17 are increased. To keep the inner pressures, which are increased by the evaporating gas, below a prescribed pressure, safety valves 40 and 42 are provided and the evaporating gas is discharged through the filter 37 to get rid of foul odor.

As shown in FIG. 3, the tissue piece treating apparatus 10 has a control section 38 for controlling the rotary valve 30, the open/close valve 32 and the pump 34. The control section 38 firstly immerses the tissue pieces, which have been accommodated in the processing chamber 12, in ethanol so as to replace moisture and fat in the tissue pieces by ethanol.

Figure 4:
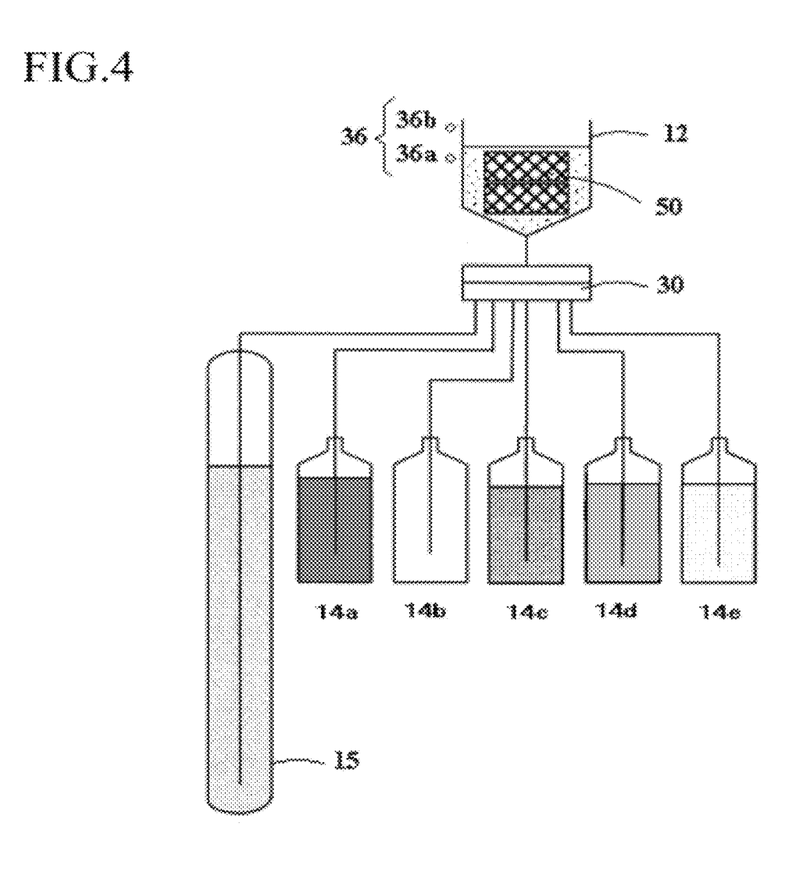
[FIG. 4] It is an explanation view of the apparatus shown in FIGS. 1A and 1B, which explains a normal treatment operation.

The control action of the control section 38 will be explained with reference to FIG. 4. In FIG. 4, the chemical tanks 14a-14e store ethanol, and concentrations of the ethanol stored in the chemical tanks are 14a<14b<14c<14d<14e.

In FIG. 4, the tissue pieces, which have been stored in a basket 50 accommodated in the processing chamber 12, are immersed in the ethanol with the lowest concentration, which has been supplied from the chemical tank 14a, and then ethanol is supplied to the processing chamber 12 from the chemical tank 14b, which is selected by the rotary valve 30 driven by a signal sent from the control section 38. The ethanol is supplied by the steps of: sending a signal from the control section 38 to the pump 34 (see FIG. 3) so as to reduce the inner pressure of the processing chamber 12; and then connecting the rotary valve 30 to the pipe 33 by the open/close valve 32 (see FIG. 3) driven by the signal sent from the control section 38, so that the ethanol stored in the chemical tank 14b can be supplied to the processing chamber 12. The level of the ethanol supplied into the chemical tank 14b is between the level-securing sensor 36a and the upper limit sensor 36b, and the amount of the ethanol is capable of fully immersing the tissue pieces in the ethanol.

When the tissue pieces are immersed in the ethanol, the rotary valve 30 is disconnected from the pipes 31 and 33.

In this state, the tissue pieces are immersed in the ethanol for a prescribed time, and then the pump 34 is driven by a signal from the control section 38 so as to increase the inner pressure of the processing chamber 12, the rotary valve 30 is connected to the pipe 31 by the open/close valve 32 driven by a signal from the control section 38, so that the ethanol in the processing chamber 12 can be returned to the chemical tank 14b.

Further, the ethanol stored in the chemical tanks 14c, 14d and 14e are sequentially supplied to the processing chamber 12, as well, so as to replace moisture and fat in the tissue pieces by ethanol.

The tissue pieces, in which moisture and fat have been replaced by ethanol, are sequentially immersed in xylene supplied from the chemical tanks 16a-16f to the processing chamber 12, as well as the ethanol treatment operations, so as to replace ethanol by xylene, and then molten paraffin stored in the chemical tanks 18a-18d are sequentially supplied to the processing chamber 12, as well as the xylene treatment operations, so as to replace xylene in the tissue pieces by paraffin.

In case that the immersing treatment of the tissue pieces is repeatedly performed, the amount of ethanol in the chemical tank will be insufficient due to evaporation and impregnation into the tissue pieces.

Figure 5A:
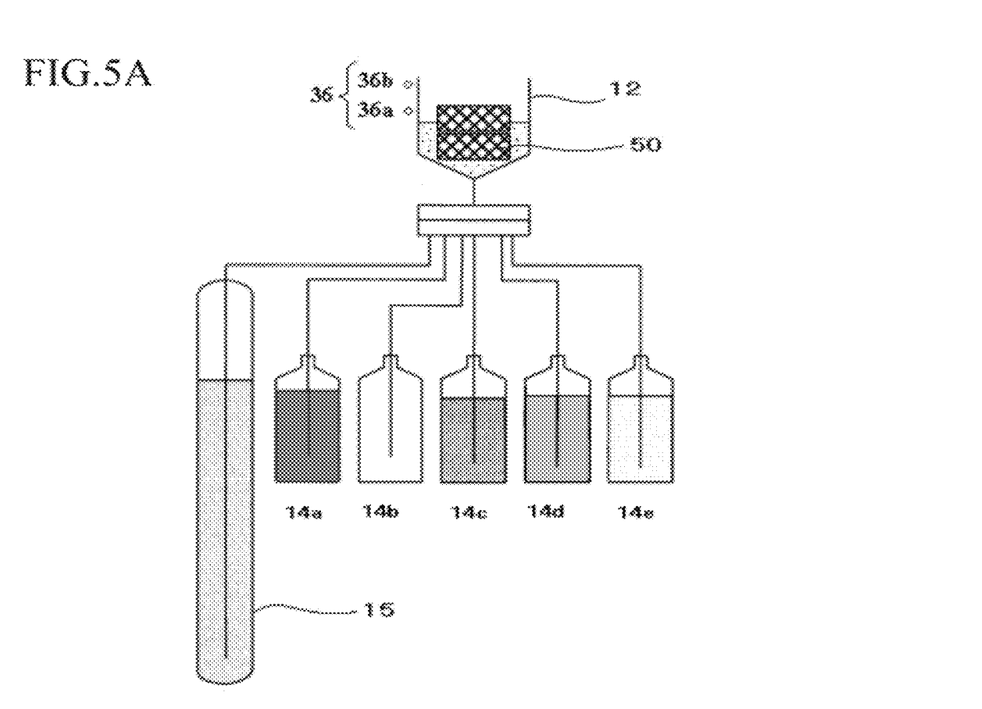
FIGS. 5A and 5B are explanation views which show a manner of refilling a processing chamber 12 with a chemical when the chemical in the processing chamber is insufficient.

For example, as shown in FIG. 5A, in case that the level of ethanol in the processing chamber 12 does not reach the level-securing sensor 36a when the ethanol is supplied from the chemical tank 14b to the processing chamber 12, the level-securing sensor 36a sends an insufficient signal to the control section 38. Upon receiving the insufficient signal, the control section 38 sends a drive signal to the rotary valve 30 so as to connect the new chemical tank 15 to the open/close valve 32 and the pipe 33, so that new ethanol stored in the new chemical tank 15 is supplied, as shown in FIG. 5, until the level of the ethanol in the processing chamber 12 reaches the level-securing sensor 36a. At that time, the open/close valve 54 provided to the pressure equalizing line is closed.

When the level of the ethanol reaches the level-securing sensor 36a, the immersion treatment of the tissue pieces can be performed.

After the immersion treatment of the tissue pieces is performed for a prescribed time, the pump 34 is driven by a signal from the control section 38 so as to increase the inner pressure of the processing chamber 12, and the rotary valve 30 is connected to the pipe 31 by the open/close valve 32 driven by a signal from the control section 38, so that the ethanol in the processing chamber 12 can be returned to the chemical tank 14b. A prescribed amount of ethanol to be supplied to the processing chamber 12 is stored in the chemical tank 14b.

Next, the immersion treatment of the tissue pieces with the ethanol stored in the chemical tanks 14c-14e are performed as well.

Further, in case that the amount of xylene supplied from the prescribed chemical tank to the processing chamber 12 for the xylene treatment is insufficient, the control section 38 sends the drive signal to the rotary valve 30 so as to connect the new chemical tank 17 to the open/close valve 32 and the pipe 33, so that new ethanol stored in the new chemical tank 17 is supplied until the level of the ethanol in the processing chamber 12 reaches the level-securing sensor 36a so as to perform the immersion treatment for a prescribed time. At that time, the open/close valve 56 provided to the pressure equalizing line is closed.

Figure 5B:
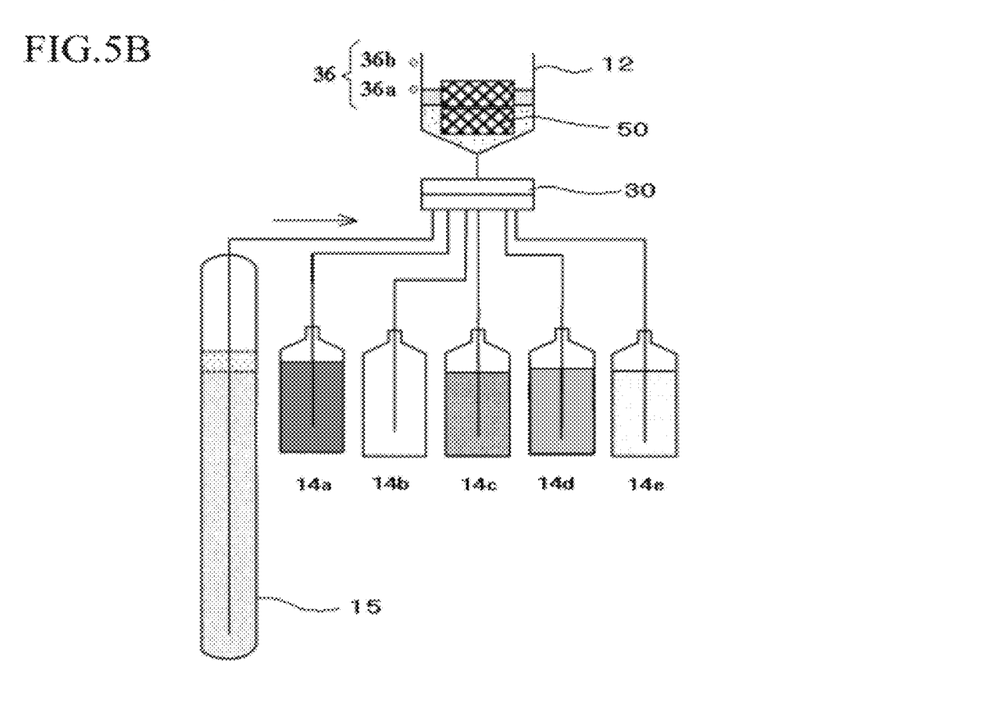

As shown in FIGS. 5A and 5B, in case that the amount of ethanol supplied to the processing chamber 12 from any of the chemical tanks 14a-14e is insufficient, the processing chamber is refilled with the ethanol stored in the new chemical tank 15, namely the insufficient ethanol can be easily refilled.

Note that, by refilling with the ethanol stored in the new chemical tank 15, concentration gradient of the ethanol stored in the chemical tanks 14a-14e is varied.

Figure 6A:
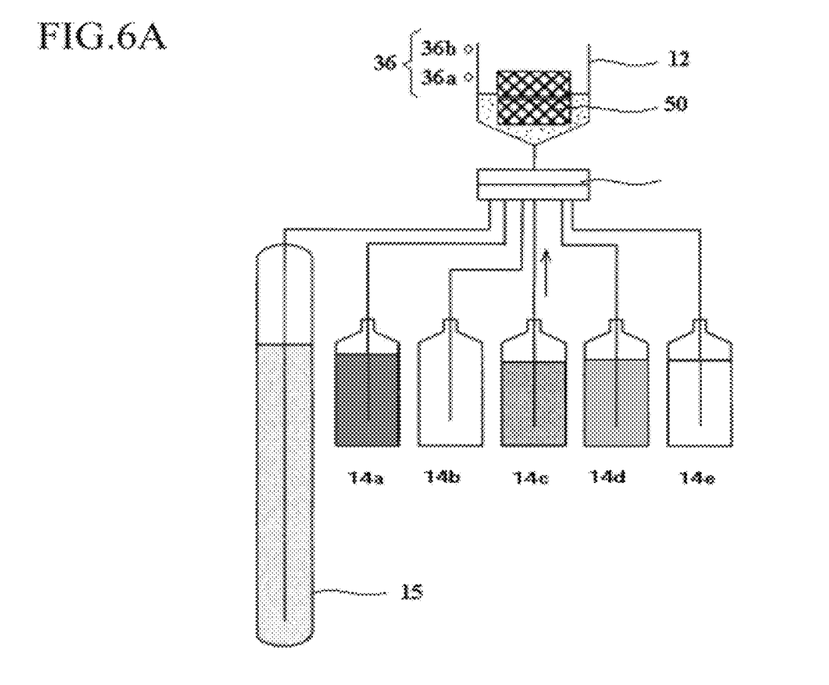
FIGS. 6A and 6B are explanation views which show another manner of refilling the processing chamber 12 with the chemical when the chemical in the processing chamber is insufficient.

Thus, when the amount of ethanol supplied to the processing chamber 12 is insufficient, as shown in FIG. 6A, and the level-securing sensor 36a sends the insufficient signal to the control section 38, the control section 38 drives the rotary valve 30 so as to connect the chemical tank 14c to the open/close valve 32 and the pipe 33 as shown in FIG. 6A.

Therefore, the ethanol, which is stored in the chemical tank 14c and whose concentration is higher than and proximate to that of the ethanol in the processing chamber 12, is supplied to the processing chamber 12 so as to perform the immersion treatment of the tissue pieces.

By supplying a part of the ethanol stored in the chemical tank 14c to the ethanol supplied from the chemical tank 14b, the amount of ethanol stored in the chemical tank 14c is insufficient when the immersion treatment of the tissue pieces is performed with the ethanol stored in the chemical tank 14c, so a part of the ethanol stored in the chemical tank 14d is supplied thereto.

Next, when the immersion treatment is performed with the ethanol stored in the chemical tank 14d, the amount of ethanol stored in the chemical tank 14d is insufficient, so a part of the ethanol stored in the chemical tank 14e is supplied thereto.

Figure 6B:
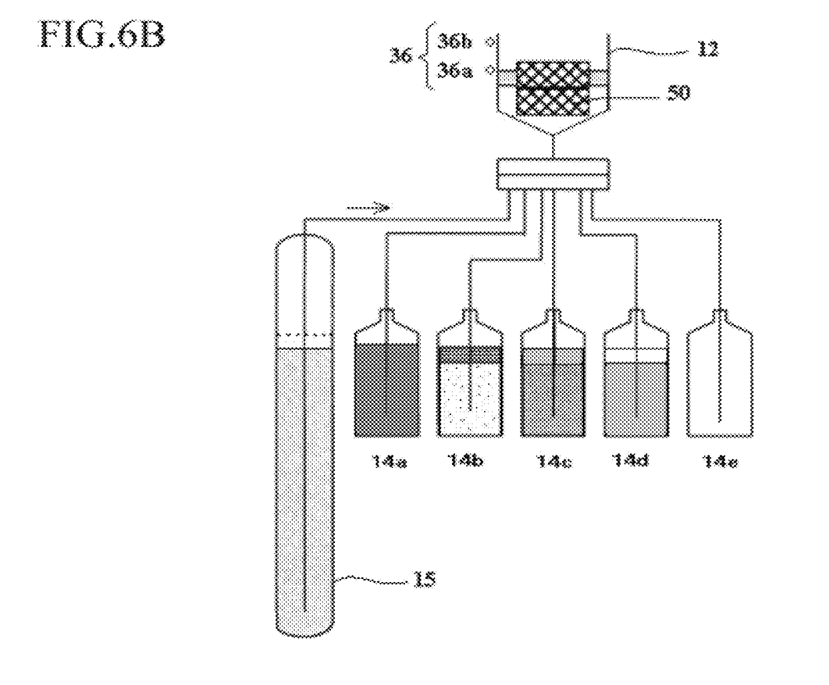

Further, when the immersion treatment is performed with the ethanol stored in the final chemical tank 14e, the chemical tank is refilled with the ethanol stored in the new chemical tank 15 as shown in FIG. 6B.

As shown in FIGS. 6A and 6B, when the amount of the ethanol in the processing chamber 12 is insufficient, the ethanol whose concentration is higher than and proximate to the ethanol in the processing chamber 12 is supplied to the processing chamber 12 from the chemical tank, so that the concentration gradient of the ethanol stored in the chemical tanks 14a-14e can be maintained.

Next, in case of performing the immersion treatment with xylene too, when the amount of the xylene in the processing chamber 12 is insufficient, the xylene whose concentration is higher than and proximate to the xylene in the processing chamber 12 is supplied to the processing chamber 12 from the chemical tank, so that the concentration gradient of the xylene stored in the chemical tanks 16a-16f can be maintained.

Note that, when the immersion treatment is performed with the xylene stored in the final chemical tank 16f, the chemical tank is refilled with the xylene stored in the new chemical tank 17.

In the tissue piece treating apparatus 10 shown in FIGS. 1A, 1B-3, the concentrations of the ethanol and the xylene stored in the chemical tanks are made lower than predetermined concentrations or impurities are included in the ethanol and the xylene by repeating the immersion treatment operations of tissue pieces. The chemical with the lowest concentration is discharged from the chemical tank, and each of the chemicals stored in the chemical tank is sequentially transferred to the chemical tank of the chemical whose concentration is lower than and proximate to that of the chemical to be transferred, this transferring operation is periodically performed.

Figure 7A:
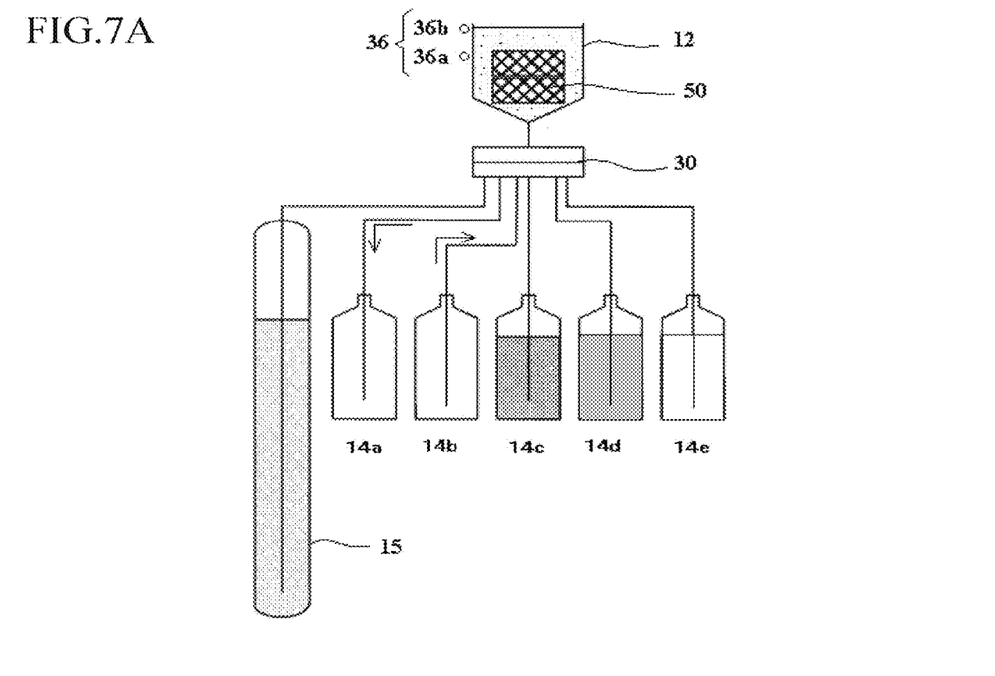
FIGS. 7A and 7B are explanation views which show a manner of transferring chemicals.

The transferring operation relating to the chemical tanks 14a-14e storing ethanol will be explained. Firstly, the chemical tank 14a, in which the ethanol with the lowest concentration is stored, is detached from the main body, a vacant chemical tank 14a is attached to the main body, and then all of the ethanol stored in the chemical tank 14b, whose concentration is higher than and proximate to that of the ethanol stored in the detached chemical tank 14a, is supplied to the processing chamber 12 as shown in FIG. 7A. In this operation, the ethanol is supplied, from the chemical tank 14b, until the upper limit sensor 36b detects the ethanol, and then the tissue pieces are immersed therein for a prescribed time.

The ethanol which has been used for the immersion treatment is transferred from the processing chamber 12 to the vacant chemical tank 14a by the rotary valve 30 which is driven by the signal sent from the control section 38. Therefore, the ethanol stored in the chemical tank 14b can be transferred to the chemical tank 14a as the ethanol with concentration of one step lower.

Further, the ethanol stored in the chemical tank 14c is transferred to the chemical tank 14b, the ethanol stored in the chemical tank 14d is transferred to the chemical tank 14d, and the ethanol stored in the chemical tank 14e is transferred to the chemical tank 14d, as well.

Then, the rotary valve 30 is driven by the signal from the control section 38 so as to supply the ethanol stored in the new chemical tank 15 to the processing chamber 12, the tissue pieces accommodated in the processing chamber 12 are immersion-treated for a prescribed time, and the ethanol is sent to the chemical tank 14e.

In the tissue piece treating apparatus 10 shown in FIGS. 1A, 1B-3, the transferring operation can be performed with performing the immersion treatment of the tissue pieces accommodated in the processing chamber 12.

Figure 7B:
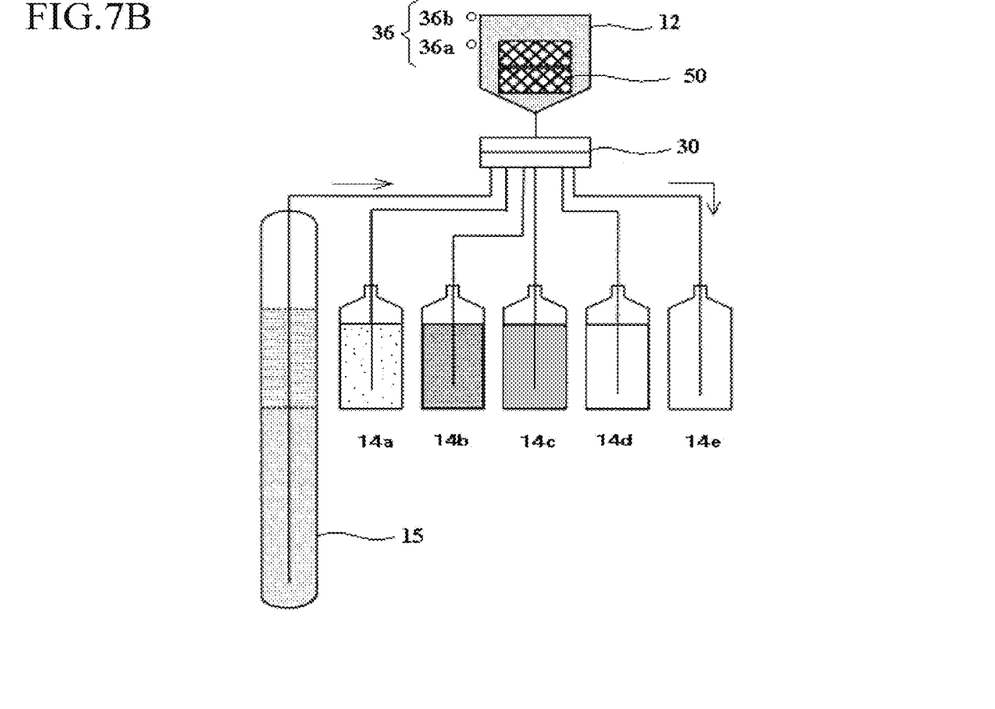

Note that, the stored xylene is also transferred between the chemical tanks 16a-16f as well as the ethanol.

In the tissue piece treating apparatus 10 shown in FIGS. 1A, 1B-3, the new chemicals stored in the new chemical tanks 15 and 17 are used, as shown in FIGS. 5A, 5B-7A and 7B, when the amount of the chemical stored in the chemical tank is insufficient or the transferring operation of the chemical is performed. Therefore, the chemicals can be easily managed, by monitoring the amounts of the chemical in the new chemical tanks 15 and 17, without monitoring the amount of each of the chemicals stored in the chemical tanks.

Note that, means for supplying new chemicals from outside is provided to each of the new chemical tanks 15 and 17. The supply ports 22 and 24 (see FIGS. 1A, 1B and 3), the pump 34 and the open/close valves 54 and 56, which are respectively provided to the pressure equalizing lines, can be used as the means for supplying new chemicals.

In case of supplying new methanol to the new chemical tank 15 storing ethanol, an external tank (not shown) storing the new methanol is connected to the supply port 24 of the main body.

Next, the pump 34 is driven and the open/close valve 54 of the pressure equalizing line is opened so as to reduce inner pressure of the new chemical tank 15, so that the new ethanol can be supplied from the external tank to the new chemical tank 15.

In case of supplying new xylene to the new chemical tank 17 storing xylene, an external tank (not shown) storing the new xylene is connected to the supply port 22 of the main body, and then the pump 34 is driven and the open/close valve 56 of the pressure equalizing line is opened so as to reduce inner pressure of the new chemical tank 17, so that the new xylene can be supplied from the external tank to the new chemical tank 17.

In case that the inner pressure of the new chemical tanks 15 and 17 are reduced by the pump 34 when the new chemicals are supplied to the new chemical tanks 15 and 17, the pressure reducing operations must be performed while the treatment operations of the tissue piece treating apparatus 10 is stopped. To independently supply the new chemicals to the new chemical tanks 15 and 17 while the tissue piece treating apparatus 10 performs the treatment operations, it is desirable to use the means for supplying the new chemicals shown in FIG. 8.

Figure 8:
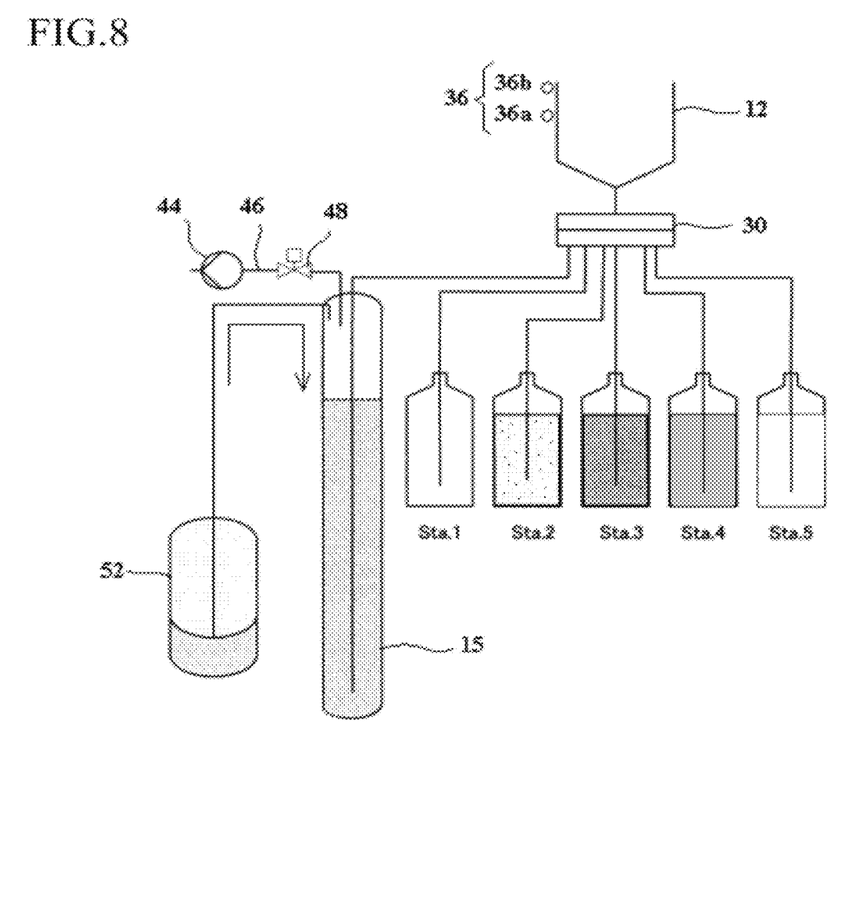
[FIG. 8] It is an explanation view of means for solely supplying a new chemical to a new chemical tank 15.

In the means for supplying the new chemicals shown in FIG. 8, an air pump 44 and an open/close valve 48 are provided to a tube 46 whose one end is inserted in the new chemical tank 15, ethanol stored in an external tank 52 is sucked and introduced toward the new chemical tank 15 whose inner pressure is reduced by the air pump 44, so that the new ethanol can be easily supplied to the new chemical tank 15.

Further, as to the new chemical tank 17, another air pump is provided, xylene stored in an external tank is sucked and introduced toward the new chemical tank 17 whose inner pressure is reduced by the air pump, so that the new xylene can be easily supplied to the new chemical tank 17.

What is claimed is:

1. A tissue piece treating apparatus comprising:
   a processing chamber for accommodating a tissue piece;
   a plurality of chemical tanks storing chemicals with sequentially different concentrations for performing immersion treatment of the tissue piece;
   a selection valve for connecting the processing chamber to the selected chemical tank;
   an open/close valve being provided to a pipe connecting the selection valve to the processing chamber so as to open/close the pipe;
   a pump for increasing and reducing inner pressure of the processing chamber;
   a detection sensor for detecting that a prescribed amount of the chemical is supplied to the processing chamber; and
   a control section being attached to a main body of said apparatus, the control section controlling the selection valve, the open/close valve and the pump so as to supply the chemical stored in the selected chemical tank to the processing chamber, whose inner pressure has been reduced by the pump, via the open/close valve and so as to discharge the chemical, which has been used for performing immersion treatment of the tissue piece, from the processing chamber, whose inner pressure has been increased by the pump, and return the same to the selected chemical tank via the selection valve, thereby the immersion treatment of the tissue piece can be performed in the chemicals from the lowest concentration to the highest concentration sequentially,
   wherein new chemical tanks are integrally attached to a sidewall face of the main body, the new chemical tanks have larger capacities than the chemical tanks, store unused new chemicals of the same types as the chemicals stored in the chemical tanks and have inner wall faces respectively reinforced by reinforcing members so as to prevent deformation of the new chemical tanks when inner pressure is reduced and increased for supplying and discharging the new chemical,
   pipes from the new chemical tanks are connected to the selection valve so as to supply the new chemicals stored in the new chemical tanks to the processing chamber, and
   the control section controls the selection valve, the open/close valve and the pump so as to supply the new chemical of an amount corresponding to an insufficiency of the amount of the chemical from the new chemical tank to the processing chamber when a detection sensor detects that the amount of the chemical supplied to the processing chamber is insufficient, thereby the immersion treatment can be continued.

2. The tissue piece treating apparatus according to claim 1, wherein the control section controls the selection valve, the open/close valve and the pump so as to supply the chemical, whose concentration is higher than and proximate to that of the chemical in the processing chamber and whose amount corresponds to an insufficiency of the amount of the chemical in the processing chamber, from the chemical tank to the processing chamber when the detection sensor detects that the amount of the chemical supplied to the processing chamber is insufficient, to continue the immersion treatment, and so as to supply the new chemical of the amount corresponding to an insufficiency of the amount of the chemical in the processing chamber from the new chemical tank to the processing chamber when the chemical with the highest concentration is supplied from the chemical tank to the processing chamber and the detection sensor detects that the amount of the chemical supplied to the processing chamber is insufficient.

thereby the immersion treatment can be continued.

3. The tissue piece treating apparatus according to claim 2, wherein the control section controls the selection valve, the open/close valve and the pump so as to return the chemical, to which the chemical or new chemical of the amount corresponding to the insufficiency has been added and in which the immersing treatment of the tissue piece has been performed, to the chemical tank of the insufficient chemical.

4. The tissue piece treating apparatus according to claim 3, wherein the control section controls the selection valve, the open/close valve and the pump so as to sequentially supply the chemicals stored in the chemical tanks to the processing chamber, in which the tissue piece is accommodated, according to the treatment process, to perform the immersion treatment of the tissue piece, sequentially transfer the chemicals to the predetermined chemical tanks, supply the new chemical stored in the new chemical tank to the processing chamber to perform the immersion treatment of the tissue piece and then transfer the new chemical, which has been used for the immersion treatment, to the chemical tank of the chemical with the highest concentration, when the chemical with the lowest concentration is discharged from the chemical tank and each of the chemicals stored in the chemical tank is sequentially transferred to the chemical tank of the chemical whose concentration is lower than and proximate to that of the chemical to he transferred.

5. The tissue piece treating apparatus according to claim 2, wherein the control section controls the selection valve, the open/close valve and the pump so as to sequentially supply the chemicals stored in the chemical tanks to the processing chamber, in which the tissue piece is accommodated, according to the treatment process, to perform the immersion treatment of the tissue piece, sequentially transfer the chemicals to the predetermined chemical tanks, supply the new chemical stored in the new chemical tank to the processing chamber to perform the immersion treatment of the tissue piece and then transfer the new chemical, which has been used for the immersion treatment, to the chemical tank of the chemical with the highest concentration, when the chemical with the lowest concentration is discharged from the chemical tank and each of the chemicals stored in the chemical tank is sequentially transferred to the chemical tank of the chemical whose concentration is lower than and proximate to that of the chemical to be transferred.

6. The tissue piece treating apparatus according to claim 1, wherein the control section controls the selection valve, the open/close valve and the pump so as to return the chemical, to which the chemical or new chemical of the amount corresponding to the insufficiency has been added and in which the immersing treatment of the tissue piece has been performed, to the chemical tank of the insufficient chemical.

7. The tissue piece treating apparatus according to claim 6, wherein the control section controls the selection valve, the open/close valve and the pump so as to sequentially supply the chemicals stored in the chemical tanks to the processing chamber, in which the tissue piece is accommodated, according to the treatment process, to perform the immersion treatment of the tissue piece, sequentially transfer the chemicals to the predetermined chemical tanks, supply the new chemical stored in the new chemical tank to the processing chamber to perform the immersion treatment of the tissue piece and then transfer the new chemical, which has been used for the immersion treatment, to the chemical tank of the chemical with the highest concentration, when the chemical with the lowest concentration is discharged from the chemical tank and each of the chemicals stored in the chemical tank is sequentially transferred to the chemical tank of the chemical whose concentration is lower than and proximate to that of the chemical to be transferred.

8. The tissue piece treating apparatus according to claim 1, wherein the control section controls the selection valve, the open/close valve and the pump so as to sequentially supply the chemicals stored in the chemical tanks to the processing chamber, in which the tissue piece is accommodated, according to the treatment process, to perform the immersion treatment of the tissue piece, sequentially transfer the chemicals to the predetermined chemical tanks, supply the new chemical stored in the new chemical tank to the processing chamber to perform the immersion treatment of the tissue piece and then transfer the new chemical, which has been used for the immersion treatment, to the chemical tank of the chemical with the highest concentration, when the chemical with the lowest concentration is discharged from the chemical tank and each of the chemicals stored in the chemical tank is sequentially transferred to the chemical tank of the chemical whose concentration is lower than and proximate to that of the chemical to be transferred.

* * * * *